(12) United States Patent
Sternoff et al.

(10) Patent No.: US 9,393,261 B2
(45) Date of Patent: Jul. 19, 2016

(54) ANTIMICROBIAL ANTI-CHAFING CHELATED SILVER OXIDE COMPOUND

(75) Inventors: William R. Sternoff, Bellevue, WA (US); William Wingfield, Richmond, VA (US); Frank Reed, Moorestown, NJ (US)

(73) Assignee: Body Glide LLC, Bellevue, WA (US)

( * ) Notice: Subject to any disclaimer, the term of this patent is extended or adjusted under 35 U.S.C. 154(b) by 145 days.

(21) Appl. No.: 13/188,630

(22) Filed: Jul. 22, 2011

(65) Prior Publication Data

US 2013/0022643 A1 Jan. 24, 2013

(51) Int. Cl.
| | | |
|---|---|---|
| *A61K 31/722* | (2006.01) | |
| *A61K 9/06* | (2006.01) | |
| *A61K 9/00* | (2006.01) | |
| *A61K 31/4166* | (2006.01) | |
| *A61K 33/38* | (2006.01) | |

(52) U.S. Cl.
CPC ............. *A61K 31/722* (2013.01); *A61K 9/0014* (2013.01); *A61K 9/06* (2013.01); *A61K 31/4166* (2013.01); *A61K 33/38* (2013.01)

(58) Field of Classification Search
USPC ........................................... 424/400; 514/55
See application file for complete search history.

(56) References Cited

U.S. PATENT DOCUMENTS

| | | | | |
|---|---|---|---|---|
| 1,482,906 | A | * | 2/1924 | Allen .............................. 424/489 |
| 4,847,049 | A | | 7/1989 | Yamamoto |
| 5,057,542 | A | * | 10/1991 | Leuba et al. ..................... 514/55 |
| 5,676,977 | A | | 10/1997 | Antelman |
| 5,895,782 | A | | 4/1999 | Overton |
| 6,130,321 | A | * | 10/2000 | Johnson et al. .................. 536/20 |
| 6,258,385 | B1 | | 7/2001 | Antelman |
| 6,583,176 | B2 | | 6/2003 | Arata |
| 6,716,895 | B1 | | 4/2004 | Terry |
| 6,756,059 | B2 | | 6/2004 | Roszell |
| 6,838,095 | B2 | * | 1/2005 | Newman et al. ............... 424/618 |
| 6,881,424 | B1 | | 4/2005 | Kemp |
| 7,135,195 | B2 | | 11/2006 | Holladay |
| 7,311,927 | B2 | | 12/2007 | Miner |
| 2004/0022868 | A1 | | 2/2004 | Antelman |
| 2004/0043963 | A1 | * | 3/2004 | Wadstein ......................... 514/55 |
| 2006/0105057 | A1 | | 5/2006 | Antelman |
| 2007/0264204 | A1 | | 11/2007 | Noor |
| 2008/0045491 | A1 | | 2/2008 | Fitchmun |
| 2008/0311206 | A1 | * | 12/2008 | Student et al. ................. 424/489 |
| 2009/0035342 | A1 | * | 2/2009 | Karandikar et al. ........... 424/411 |
| 2010/0120915 | A1 | | 5/2010 | Beierle |

FOREIGN PATENT DOCUMENTS

| | | | |
|---|---|---|---|
| JP | 27230996 | A2 | 9/2007 |
| RU | 2271814 | * | 6/2005 |
| WO | 2004028461 | A2 | 4/2004 |
| WO | 2006015317 | A2 | 2/2006 |

OTHER PUBLICATIONS

Balm, Thesaurus.com, http://thesaurus.com/browse/balm, retrieved online on Jun. 10, 2013.*
Xenex Labs, Potassium Citrate Monohydrate, http://www.xenexlabs.com/catalogue.php?cid=3&pid=589, retrieved online on Jan. 14, 2014.*
Muzarelli, Solubility and Structure of N-carboxymethylchitosan, 1994, p. 1-4.*
Netafilm, Mesh vs. Micron Comparison Chart, retrieved online on Aug. 13, 2015.*
Zhigang, Hu: Suspension of Silver Oxide Nanoparticles in Chitosan Solution and its Antibacterial Activity in Cotton Fabrics. Reference Mater. Res. Soc. Symp. Proc. vol. 920 copyright 2006 Materials Research Society.
Final Report—Kill Rate Coefficient Test with MRSA, Jul. 1, 2014, Universal Laboratories, Hampton, VA, submitted to AG Essence, Richmond, VA.

* cited by examiner

*Primary Examiner* — Jennifer Berrios
(74) *Attorney, Agent, or Firm* — ePatentManager; Guerry L Grune

(57) ABSTRACT

Described herewithin is a composition comprising an anti-chafing balm with C18-36 acid triglycerides, capric/carprylic triglycerides, and tribehinin together with a chelated silver oxide complex comprising a barrier film when applied to the skin. The film is a dual purpose antibacterial and anti-chafing barrier topically applied to human skin, providing a layer of chelated silver oxide complex further comprised of a dermatologically acceptable carrier, with friction (chafe) reducing properties, selected from the group consisting of organic solutions, gels, liquids, balms, aerosols, emulsifiers, lotions, water-in-oil emulsions, oil-in-water emulsions, surfactants, aloe barbedensis leaf juice and tocopherol acetate.

12 Claims, 2 Drawing Sheets

| 10 | Prepare Chitosan |
|---|---|
|  |  |
| 11 | Provide raw material |
| 12 | Remove non-chitin components |
| 13 | Dry and grind to desired size |
| 14 | Deacetylation |
| 15 | Rinse |

FIG. 1

| 20 | Prepare Chitosan Solution |
|---|---|
|  |  |
| 21 | Provide deionized water |
| 22 | Provide Chitosan powder |
| 23 | Provide alpha-hydroxy acid |
| 24 | Mix |

FIG. 2

| 30 | Prepare Aqueous Silver Solution |
|----|-------------------------------------|
|    |                                     |
| 31 | Provide silver salts                |
| 32 | Provide alkaline solution           |
| 33 | Create silver oxide                 |
| 34 | Provide carboxylic acid             |
| 36 | Provide deionized water             |
| 37 | Provide light impervious container  |

FIG. 3

| 40 | Prepare Antimicrobial Complex    |
|----|--------------------------------------|
|    |                                      |
| 41 | Provide Chitosan Solution            |
| 42 | Provide deionized water              |
| 43 | Provide Aqueous Chelated Silver Solution |
| 44 | Mix until homogenous                 |

FIG. 4

ANTIMICROBIAL ANTI-CHAFING CHELATED SILVER OXIDE COMPOUND

PRIORITY CLAIM

This application claims priority from provisional application 60/930,535 filed May 17, 2007 entitled "Antimicrobial Solution and Methods of Making and Using the Same" and assigned to William Wingfield. This application also incorporates by reference the entire contents of the same provisional application.

FIELD OF THE INVENTION

Chafing is a friction-induced injury to the skin, ranging from minor irritation or abrasion, to a wound where layers of the skin are worn away, or ruptured. Moisture, salts and minerals excreted as perspiration often aggravate, accelerate and exasperate chafing. The effects of chafing are seen, for example, as rash, redness, tearing or scraping of the skin, or a wound open to possible infection. Use of compounds to soothe skin and alleviate chafing is well known, and there have been a variety of products available on the market to perform the required function. Perspiration is not only an aggravating factor in chafing, but is associated with growth and spread of bacteria, microorganisms or "germs", that spread from person to person as, for example, among athletes (such as, and including wrestlers). Such germs may cause irritation and skin disease, and where skin is opened by chafing, germs can enter the body. The present invention relates to an antimicrobial, anti-chafing barrier compound which includes a chelated silver oxide complex, and in particular, to adding this complex to anti-chafing compounds to create complexed silver oxide based antimicrobial and anti-chafing compounds, and to the methods of making the same.

BACKGROUND OF THE INVENTION

Chafing occurs where skin rubs against skin, clothing, shoes, or other materials. Chafing occurs where heals of shoes scrape the back of the foot, in folds of skin or where thighs rub each other or are rubbed by clothing, where repetitive rubbing causes noticeable and painful heat, such as when walking or running. Skin chafing is an everyday problem typically experienced by anyone whose body is in motion (in some instances, at rest), whether at work, in sports, or for example, people in the armed services. The U.S. Army has contracted with companies to develop and provide special apparel with low friction fiber technology to integrate into various components of the soldier's uniform, for the sole purpose of reducing chafing of the skin. Skin chafing is also a problem in infants in the form of "diaper rash." "Diaper rash" has been defined by the U.S. Food and Drug Administration as an inflammatory skin condition in the diaper area (perineum, buttocks, lower abdomen, and inner thighs) caused by factors including chaffing or mechanical agitation.

Solutions to the chafing problem found in the relevant art range from applications of lubricants (such as petroleum jelly, or use of talcum powder on the affected areas of the skin to temporarily alleviate the irritation), to wearing certain apparel, such as spandex and nylon, to guard against chafing caused when body parts rub together. The application of some formulae, may themselves cause forms of skin irritation, such as petrolatum, petroleum jelly, lanolin, and certain other ingredients that may cause allergic or other problems for some individuals. Some formulae ingredients may interfere with perspiration or leave a greasy or messy residue. Special formulations have been developed such as BODYGLIDE® skin formulae, that address chafing, allow perspiration, are non-greasy, and are hypoallergenic.

Because chafed skin is vulnerable to bacteria, fungus and microorganisms ("germs"), there is a need for a dual purpose, topical anti-chafing skin protectant barrier with antimicrobial properties.

Applicants have found that chelated silver oxide that is complexed into an anti-chafing film or compound, exhibits the needed unique characteristics combining lubricity, thermal conductivity, and antimicrobial properties to provide a compound meeting the dual purpose criteria. The chelated silver oxide complex, which is also biocompatible, adds antimicrobial properties in the anti-chafing barrier to both help protect against friction induced skin injury and contamination by bacteria, fungi, mold, germs, and microbes in the presence of perspiration or if no perspiration Occurs.

Topical antimicrobial solutions, or simply antimicrobial solutions, are widely used in today's society. Some uses are prophylactic, such as when a hand sanitizer is used prior to consuming a meal. Other times, users use a topical antimicrobial solution after they may have encountered germs and microbes prior to resuming normal activities, such as immediately after using the bathroom. This is supposed to be routine for restaurant and food preparation personnel.

Hospital acquired infections due to bacteria cause approximately more than 100,000 deaths annually. This number is more than the combined death total resulting from AIDS, breast cancer and automobile accidents. The economic burden is estimated to be greater than $5.2 billion annually. These infections are the fourth leading cause of death. Inadequate hand hygiene also contributes to food-related illnesses, including salmonella and E coli infection. According to The Center for Disease Control and Prevention (hereafter, the "CDC"), as many as 76 million Americans contract a food-borne illness each year. Of these, nearly 5,000 die as a result of the illness. Others experience the annoying symptoms of nausea, vomiting and diarrhea.

Published CDC guidelines enhanced hand sanitizer sales in the United States, which experienced double-digit growth in the 2004-2010 period, according to marketing information provided by A.C. Nielsen. The total annual U.S. infection prevention industry is $9.4 billion.

Some antimicrobial agents utilize bleach or other chemicals that can have harsh and unintended consequences on a user's skin.

Silver is a naturally occurring element that is present in our environment, including the air we breathe, the water we drink and the foods we consume. However, silver does not occur naturally in the tissues of humans and animals. Silver exhibits relatively low toxicity to animals and humans. It is however, extremely toxic to simpler forms of life such as bacteria. The antibacterial properties of silver are known, and were at least suspected for thousands of years. The ancient Greeks used silver pots and other utensils. Hippocrates, the father of modern medicine, wrote that silver had beneficial healing and anti-disease properties. The Phoenicians stored water, wine and vinegar in silver bottles to prevent spoiling. In the early 1900s, it was not uncommon for people to place silver dollars in milk bottles to prolong the freshness of the milk. The malleability and non-toxicity of silver make it a useful material used in dental alloys for fittings and fillings.

Widespread use of silver declined with the development of modern antibiotics, many of them used to kill pathogens, but overuse has led to increased bacteria resistance. Hence, there is renewed interest in silver as a broad spectrum antimicrobial. Silver, when applied topically, demonstrates efficacy against microorganisms which sometimes exhibit resistance characteristics. There are many products on the market to treat or kill bacteria. These products are found in a variety of forms, including liquid, foam, gel, lotions and ointments. Some of these products are described in the following patents:

RELEVANT ART

U.S. Pat. No. (Hereafter, "USP") 4,847,049 to Yamamoto and entitled "Method of Forming Chelated Collagen Having Bactericidal Properties" describes a method for protecting renatured collagen against bacterial and fungal attack. The method includes contacting the collagen with a silver ion containing solution at a pH range of 4.0 to 9.0 and exposing the silver-chelated collagen to ultraviolet radiation.

U.S. Pat. No. 6,756,059 to Rozell et al. and entitled "Topical Composition, Topical Composition Precursor, and Methods for Manufacturing and Using" discloses a topical composition precursor prepared by melt processing a hydrophobic polymer composition that includes repeating pyrrolidone/alkylene groups wherein the alkylene groups contain at least 10 carbon atoms, and a hydrophobic polymer composition including repeating carboxylic groups and/or hydroxyl groups.

U.S. Pat. No. 6,716,895 to Terry entitled "Polymer Compositions Containing Colloids of Silver Salts" teaches how to provide varying release kinetics for the active ions in the compositions due to different water solubilities of the ions, allowing antimicrobial release tailored to a given application. The polymer compositions are stated to contain colloids comprised of salts of one or more oligodynamic metals such as silver.

U.S. Pat. No. 7,135,195 to Holladay et al. entitled "Treatment of Humans with Colloidal Silver Composition" describes water and silver particles, wherein the silver particles comprise an interior of elemental silver and an exterior of ionic silver oxide. The silver particles are described to be present in the water at a level of about 5-40 parts per million (Hereafter, "ppm").

U.S. Pat. No. 6,881,424 to Kemp entitled "Highly Acidic Metalated Organic Acid" teaches how to mix a monovalent or polyvalent cation and an organic acid in the presence of a strong oxyacid. The resulting composition is described to be less corrosive to a ferrous metal than a solution of a mineral acid having the same acidic pH value, and is more biocidal than a mixture of the organic acid and a metal salt of the organic acid which mixture has the same acid normality value.

U.S. Pat. No. 5,895,782 to Overton et al. is entitled "Acid Replacement Solution for Cleaning of Non Ferrous Metals" describes the use of non-ferrous alloys such as copper, brass and high strength aluminum alloys for cleaning purposes. The solution is described to be prepared by mixing $Ca(OH)_2$ and KOH with equivalent sulfuric acid in water, and then passing the solution through a 10 micron filter.

U.S. Pat. No. 6,383,095 to Newman, et al. is entitled "Ionic Silver Complex" and describes how to combine ingredients including water, a source of free silver ions, and a substantially non-toxic, substantially thiol-free, substantially water soluble complexing agent. This patent claims the use of an alkali metal and/or alkaline earth metal used as a counter-ion.

U.S. Pat. No. 6,583,176 to Arata is entitled "Aqueous Disinfectant" and describes an aqueous solution that is formulated by electrolytically generating silver ions in water in combination with a citric acid.

Japanese patent application JP 2007230996A2 (Abstract only) and entitled "Anti-chafing composition comprising Boron Nitride" to General Electric Co., describes an anti-chafing composition for topical application comprising boron nitride.

US Patent Application No. 20080311206A1 entitled "Anti-Chafing Compositions Comprising Boron Nitride" to Student, et al. and assigned to General Electric Co., describes an anti-chafing composition for topical application comprising boron nitride.

U.S. Pat. No. 5,676,977 entitled "Method of Curing AIDS with Tetrasilver Tetroxide Molecular Crystal Devices" to Antelman and assigned to Antelman Technologies Ltd. describes a method of curing the AIDS virus using an intravenous injection using Tetrasilver Tetroxide.

Korean Patent Application KR7090732A—entitled "Anti-chafing compositions comprising Boron Nitride" to Student, et al. and assigned to General Electric Co., describes an anti-chafing composition for topical application.

U.S. Pat. No. 6,258,385 entitled "Tetrasilver Tetroxide Treatment for Skin Conditions to Antelman and assigned to Marantech Holding, LLC describes an invention that relates to the use of electron active molecular crystals comprising tetrasilver tetroxide ($Ag_4O_4$) for the treatment and cure of dermatological skin conditions.

US Application Number US20060105057 entitled "Compositions Using Tetrasilver Tetroxide and Methods for Management of Skin Conditions Using Same" to Antelman and assigned to Marantech Holding, LLC., describes pharmaceutical compositions including tetrasilver tetroxide ($Ag_4O_4$), such as in crystalline form, and methods of using such compositions for the prevention, treatment, and management of various dermatological skin conditions and diseases to include but not limited to skin chafing.

US Application Number US20040022868 entitled "Compositions Using Tetrasilver Tetroxide and Methods for Management of Skin Conditions Using Same" to Antelman and assigned Marantech Holding, LLC describes pharmaceutical compositions including tetrasilver tetroxide (Ag4O4), such as in crystalline form, and methods of using such compositions for the prevention, treatment, and management of various dermatological skin conditions and diseases to include but not limited to skin chafing.

US Application Number 20100120915A1 entitled "Antimicrobials and Related Methods to Beierle and not assigned, describes antimicrobial balms but does not mention the use of any type of silver or silver ions).

U.S. Pat. No. 7,311,927 entitled "Antiseptic Solutions Containing Silver Chelated with Polypectate and EDTA" to Miner, et al and assigned to Edwin Odell Miner, describes a liquid antiseptic and cleanser having improved long-term stability and includes silver ion in the list of ingredients.

PCT Publication Number WO2004/028461 entitled "Antiseptic Solutions Containing Silver Chelated with Polypectate and EDTA" by Miner, et al, describes a liquid antiseptic and cleanser having improved long-term stability and includes silver ions in the list of ingredients.

A PCT application to Karandiakar, WO 2006/015317, entitled "Antimicrobial Devices and Compositions" describes methods and compositions for antimicrobial devices comprising metal containing compositions which are resistant to heat and light discoloration. The metal containing compositions may comprise salts or complexes of silver, copper or zinc. In one aspect the compositions comprise silver salts. In another aspect, the compositions comprise silver complexes. In one aspect, the metal salts may comprise metal salts of saccharin, acesulfame, long chain fatty acids, and alkyl dicarboxylic acids. The compositions further comprise polymers which form salts or complexes with silver, copper or zinc. The methods of the present invention comprise treating devices with the metal containing compositions, including, but not limited to, such devices as woven wound care materials, catheters, patient care devices, and collagen matrices. A U.S. patent to Newman, U.S. Pat. No. 6,830,895, entitled "Ionic Silver Oxide Complex" describes an invention that relates to a substantially non-colloidal solution made by combining ingredients comprising (a) water; (b) a source of free silver ions; and (c) a substantially non-toxic, substantially thiol-free, substantially water-soluble complexing agent.

The patents or patents pending described above do not incorporate the use of a chelated silver oxide complex as described here within to form an antibacterial compound or barrier to chafing of the skin that effectively kills bacteria for extended periods of time.

It is an object of the present invention to provide an antimicrobial anti-chafing chelated silver oxide barrier compound having relatively long term effectiveness.

It is another object of the present invention to provide an antimicrobial anti-chafing barrier compound having high residual effectiveness.

It is a further object of the present invention to provide an antimicrobial anti-chafing barrier compound that readily adheres to a user's surface skin cells.

It is a still further object of the present invention to provide an antimicrobial and anti-chafing barrier compound that is stable, portable and easily dispensable.

It is a still further object yet of the present invention to provide an antimicrobial anti-chafing barrier compound that is gentle, non-comedogenic (won't clog pores), hypoallergenic (won't provide allergic skin reactions), and that does not otherwise provide harsh consequences for a user's skin.

DESCRIPTION OF THE INVENTION

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases.

As used herein, the term "anti-chafing composition" means any topically applied composition of ingredients capable of reducing, relieving, or minimizing chafing from friction of human skin, particularly friction induced injury to the skin ranging from minor irritation or abrasion, to a wound where layers of the skin are worn away, or ruptured resulting from the rubbing of skin against skin, clothing, shoes, or other materials.

The term "safe and effective amount," as used herein, means an amount of a topically applied compound, component, or composition of ingredients sufficient to significantly induce a positive benefit to the user, and more particularly, as perceived by the user, a noticeable improvement, relief and/or feeling of comfort from skin irritation, providing a reasonable benefit to risk ratio, within the scope of sound medical judgment.

The term "suitable adherence to the skin" or "suitably adheres to the skin" means that the antibacterial and anti-chafing barrier composition, after being applied to the skin, adheres to the skin long enough to have an efficacious effect (as for example, for diaper rash that results from rubbing). A layer of barrier composition on the skin may be thought of as a stack of parallel thin layers, each layer being at least one molecule thick. With a composition that has suitable adherence to the skin, the composition's molecular layer closest to the skin (the bottom molecular layer) will temporarily bond physically and/or chemically to the skin on a molecular level, the composition's molecular layer above the bottom molecular layer will temporarily bond physically to that bottom molecular layer, and so on. The bonds between the skin and the bottom molecular layer and between the successive molecular layers cannot be permanent, or else it would be difficult to remove the composition from the skin. The layers, however, do form a barrier which is a temporary barrier depending on the amount of the anti-chafing composition applied to the skin. Hence, it may be desirable to provide compositional waxes, micronized waxes, corn starch, talc, or a combination of any of these substances in the final composition to provide higher viscosity and thereby lower movement of the substance once applied to the skin. All percentages and ratios used herein are by weight of the total composition and all measurements made are at 25 degrees Centigrade unless otherwise designated. Unless otherwise indicated, all percentages, ratios, and levels of ingredients referred to herein are based on the actual amount of the ingredient, and do not include solvents, fillers, or other materials which may be combined with the ingredient in commercially available products.

The antibacterial and anti-chafing barrier compositions, according to the present disclosure intended for topical application on the skin, may be in the form of a balm, stick, lotion, jelly, cream, fluid or gel distributed in any manner including an aerosol spray; pump-dispenser bottle; an atomizing spray dispenser; a roll-on; as a cream distributed in a tube; embedded in a towel or wipe; a solid wand (stick); a bar, or a powder form; and applied, wiped and/or rubbed onto the skin using the hand(s).

The antibacterial and anti-chafing compositions may comprise ingredients generally used in products of this type and well-known to those skilled in the art, provided that they do not interfere with the chelated silver oxide component as the antibacterial active ingredient described herein. The ingredients useful herein may be categorized or described herein by their benefit or their postulated mode of action. However, it is to be understood that the active and other ingredients useful herein can, in some instances, provide more than one therapeutic benefit or operate via more than one mode of action. Therefore, classifications herein are made for the sake of convenience and are not intended to limit an ingredient to the particularly-stated application or applications listed.

The total amount of chelated silver oxide complex in the finished dermatological antibacterial and anti-chafing formulation (compound) of the present invention may be varied within wide parameters, but should be in a sufficient amount for the composition to act as a barrier and/or provide a coating layer on the applied surface of the skin such that the layer suitably adheres to the skin, and in any event, the compound effectively inhibits or reduces irritation or chafing to the skin caused by rubbing, whether skin against skin or against another object including, but not limited to apparel and footwear. This amount of the antibacterial, anti-chafing compound is a chafe-reducing effective amount which provides a protective and/or mitigating benefit upon contact with the skin, the amount of which is particular to the perceived needs and results determined by the user.

Generally, in one embodiment, the chafe-reducing effective amount is in the range of 0.5 to 99.9 wt. %, based on the total weight of the formulation and the remaining amount would be the antimicrobial effective amount of the silver oxide complex.

In a second embodiment, the amount ranges from 1 wt. % to 60 wt. % of the anti-chafing compound and the remaining amount would be the antimicrobial silver oxide component effective amount and/or combined with inert ingredients.

In a third embodiment, from 5 wt. % to 40 wt. % would be anti-chafing and the remainder would be the antimicrobial silver oxide component and/or combined with inert ingredients.

In a fourth embodiment, the amount ranges from 5 to 30 wt. % as anti-chafing and the remainder would be the antimicrobial silver oxide component and/or combined with inert ingredients.

In a fifth embodiment, this amount is between 2 to 15 wt. % as anti-chafing and the remainder would be the antimicrobial silver oxide component and/or combined with inert ingredients.

For embodiments wherein the chelated silver oxide component is used in a form other than pure, in a form with a carrier ingredient as a cream, a lotion, a liquid, etc., the anti-chafing composition may also comprise at least one adjuvant chosen from waxes, softeners, antioxidants, opacifiers, stabilizers, moisturizers, vitamins, fragrances, bactericides, preserving agents, polymers, fragrances, thickeners, propellants, or any other ingredient usually used for this type of topical/dermatological application. A description of exemplary embodiments and ingredients follows.

Examples of surfactants include anionic, nonionic, and amphoteric surfactants, as long as they do not adversely interact with the ingredients used in the anti-chafing composition, nor in any way that may be irritating to the skin. Examples of nonionic surfactants include alkoxylated $C_{11}$ to $C_{22}$ fatty alkyl hydrophobes. Examples of anionics and amphoterics include betaines. In one embodiment, nonionic surfactants are used to induce gelation, thus hardening the composition if applied in the form of a stick.

The use of allantoin as an active ingredient is highly desirable. In addition, inert, non-actives can include aloe barbadensis leaf juice, C18-C36 acid triglycerides, capric/caprylictriglycerides, tocopherol acetate, and tribeherin.

In one embodiment, the antimicrobial and anti-chafing composition comprises at least one either aqueous or glycerine phase formulated, for example, in a form chosen from lotions, water-in-oil emulsions, oil-in-water emulsions, and multiple emulsions, e.g., oil-in-water-in-oil and water-in-oil-in-water triple emulsions (such emulsions are known and described, for example, by C. F. Fox in "Cosmetics and Toiletries", November 1986, Vol. 101, pages 101-112).

In one embodiment, the at least one phase comprises water and generally other water-soluble or water-miscible solvents. The water-soluble or water-miscible solvents may be chosen from short-chain monoalcohols, for example, monoalcohols of C1-C4, such as ethanol and isopropanol; and diols and polyols, for example, ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether and sorbitol. In one embodiment, the carrier vehicle comprises propylene glycol and/or glycerol. An especially useful component for preparing the antibacterial portion of the formulation is the use of propanediol.

In another embodiment, the composition comprises at least one water-immiscible organic liquid phase. The at least one water-immiscible organic phase generally comprises at least one hydrophobic compound that renders the phase water-immiscible. The at least one water-immiscible organic phase is liquid (in the absence of a structuring agent) at room temperature (20-25 degrees Centigrade).

In yet another embodiment, the at least one water-immiscible organic liquid phase is chosen from an oil and a mixture of oils and comprises at least 80% of compounds with a vapor pressure not exceeding 4 kPa (30 mmHg) at 25 degrees Centigrade. The at least one water-immiscible organic liquid phase, for example, comprises at least one emollient oil chosen from volatile and non-volatile, silicone-based, and hydrocarbon-based emollient oils. These emollient oils are, for example, described in U.S. Pat. Nos. 4,822,596 and 4,904,463.

As used herein, volatile silicones are defined, in a known manner, as being compounds that are volatile at room temperature. Mention may be made, for example, among these compounds, to cyclic and linear volatile silicones of the dimethylsiloxane type, whose chains comprise from 3 to 9 silicone-based residues. As used herein, non-volatile silicones are defined, in a known manner, as being compounds with a low vapor pressure at room temperature, such as polyalkylsiloxanes, such as linear polyalkylsiloxanes, including linear polydimethylsiloxanes, or dimethicones; polyalkylarylsiloxanes, for example, polymethylphenylsiloxanes; and copolymers of polyether and siloxane, for example, dimethicone copolyols. Among the non-volatile emollient oils that may be used, examples include hydrocarbon-based derivatives, mineral oils, fatty alcohols, esters of C3-C18 alcohols with C3-C18 acids, esters of benzoic acid with C12-C18 alcohols and mixtures thereof, C2-C2-C6 polyols, for example, chosen from glycerol, propylene glycol or sorbitol, polyalkylene glycol polymers.

Mixtures of carrier materials and/or surfactants are also usable. The total amount of carrier material employed is for some embodiments, from 10% to 99%, and for other embodiments, from 60% to 98%, expressed as a weight percentage of the total weight of the composition. The chelated silver oxide complex is normally added in amounts up to 5% by weight. Additional use of dimethicone, corn starch, talc and other mineral fillers may be utilized optionally as needed.

In a separate embodiment, the antimicrobial and anti-chafing composition(s) further include at least one other agent that imparts structure to the composition, or for gelling, at least one water-immiscible organic liquid phase of the composition, including organic structurants that are non-polymeric or polymeric. Examples of non-polymeric structurants include, but are not limited to, waxes and gellants, such as fatty acids or salts thereof, often containing from 12 to 30 carbons, such as stearic acid or sodium stearate, and/or fatty alcohols (typically insoluble in water), often containing from 12 to 30 carbons; elastomeric polyorganosiloxanes such as those described in International Patent Application WO 97/44010.

The term "fatty," as used herein, refers to a long chain aliphatic group, such as at least 8 to 12 linear carbons, which is frequently not branched (linear) and is typically saturated, but which can alternatively be branched and/or unsaturated. It is possible for the fatty acid to contain a hydroxyl group, as in 12-hydroxystearic acid, for example, as part of a gellant combination, and to employ amino or ester derivatives thereof. Examples of suitable higher molecular weight alcohols include behenyl alcohol and sterols such as lanosterol.

The waxes may be chosen from animal, fossil, plant, mineral, and synthetic waxes. Mention may be made, for example, to the use of beeswaxes, carnauba wax, candelilla wax, sugar cane wax, Japan wax, ozokerites, montan wax, microcrystalline waxes, paraffins, and silicone waxes and resins. The thickeners, which are, for example, non-ionic, may be chosen from modified and unmodified guar gums and celluloses, such as hydroxypropyl guar gum and cetylhydroxyethylcellulose.

In yet another embodiment, the antibacterial silver oxide component and anti-chafing composition further comprises stabilizers selected from particulate organic or inorganic materials, which are dispersible or dissolvable in the formulation. Examples include silica, mineral pigments, organic pigments, crosslinked polymers and copolymers of acrylic acid, cellulose ethers, and mixtures thereof. Examples of mineral pigments include, but are not limited to, calcium carbonate, titanium dioxide, clay, organophilic clay, talc, and gypsum.

In still another embodiment, wherein the antimicrobial silver oxide component and anti-chafing composition is in the form of a liquid stick, a cellulose ether, such as carboxymethyl cellulose and hydroxypropyl cellulose, is added as a structurant in concentrations of up to 10.0%. In still another embodiment, the composition comprises a solid triglyceride gellant as a structurant. The antimicrobial and anti-chafing composition can also use stearyl alcohol as a structural component in an amount of up to about 15% by weight.

The antimicrobial silver oxide component and anti-chafing composition is selected from the group consisting of polyvinyl alcohols, polyvinyl pyrrolidone, polyalkylene oxides, celluloses, cellulose derivatives, polysaccharides, polysaccharide derivatives, polycarboxylic acids, salts of polycarboxylic acids, polyamino acids, peptides, polyamides, polyacrylamides, polyesters, poly (vinyl methyl ether-co-maleic anhydride), alginates, alginate derivatives, pectins, polyethylene oxides, gelatins, carrageenans, chitosans, starches, starch derivatives, and combinations thereof.

The composition of the invention also can comprise other components that may be chosen depending on the carrier and/or the intended use of the formulation. The optional components are used in an amount that does not substantially, adversely impact the anti-chafing effect.

In a further embodiment, the anti-chafing composition further comprises a cosmetic and/or pharmacological component which functions as liquid carrier, as well as to provide soothing comfort to the body, e.g., a salicylate-based compound such as glycol salicylate and methyl salicylate, menthol, and mixtures thereof.

In one embodiment, wherein the antibacterial silver oxide component and anti-chafing composition is used as an aerosol application, the composition is used in a container/device, which further contains at least one propellant for distributing the aerosol composition.

Examples of the propellants that are generally used with the antibacterial and anti-chafing product of this type, include but are not limited to, dimethyl ether (DME); volatile hydrocarbons such as n-butane, propane or isobutane; and mixtures thereof, optionally with at least one chlorohydrocarbon and/or fluorohydrocarbon including Freon, carbon dioxide, nitrous oxide, nitrogen, or compressed air may also be used as the propellant. The anti-chafing composition and at least one propellant may be in the same compartment or in different compartments in the aerosol container. In one embodiment, the concentration of propellant generally ranges from 5% to 95% by pressurized weight and for example, from 50% to 85%, by weight relative to the total weight of the pressurized composition. In addition, aerosols are being replaced by spray cans using what is known as "bag-on-valve" methodology, where the composition is injected into a bag attached to the spray valve, and the injection compresses the air in the can which, when the valve is pressed, forces the composition to be expelled from the bag in a continuous spray (until the valve is released.) In this case, the propellant includes the use of compressed air.

In addition to the preservative nature of the chelated silver oxide complex, another embodiment includes the use of at least one preservative compound in combination with the topical anti-chafing chelated silver oxide compositional material. The preservative compounds may be present in an amount of 0.5% to about 3% by weight of the formulation. Desirably, the preservative compound is effective against yeast, particularly Candida albicans; molds, particularly Aspergillus niger; and bacteria, particularly S. aureus, E. coli, and E cloacae. Examples include disodium ethylene diamine tetraacetic acid, methylparaben, and diazolidinyl urea. The chelated silver oxide complex also serves as a chelating agent to block the activity of bacterial ureases, lipases, proteases, and decarboxylases produced by Klebsiella pneumoniae, Proteus mirabilus, and E. coli bacteria In one other embodiment, the antibacterial silver oxide component and anti-chafing composition may also include fragrances. Examples include but are not limited to citrus, floral, spicy, lavender, woody, mossy, oriental, herbal, leather-tobacco, and aldehydic groups. Typically, fragrance materials are supplied as concentrates, which generally contain up to about 3 percent fragrance by weight. Examples include natural products such as essential oils, flower oils, natural extracts from resins, gums, balsams, beans, mosses and other plants, and animal products such as ambergris and musk, as well as synthetic aromatic materials.

In further describing the embodiments of the present invention, it is desirable to provide the composition of the invention that affords in-use, lubricious, non-sticky characteristics upon application onto the skin or a surface to be in contact with the skin. When applied onto a surface such as the skin, a piece of cloth, or other surface, the composition forms a thin film over the applied surface. The applied film adheres to surface skin cells and remains substantially lubricious and non-sticky over extended periods of time after application, providing the needed results of a dual purpose barrier with antibacterial and therapeutic anti-chafing properties. When applied as a stick, a lotion, a cream, a balm, a liquid, a gel, or in powder or other form, or otherwise wiped or rubbed directly onto the skin, the antibacterial, anti-chafing composition suitably adheres to the skin as a barrier against chafing that retains its antimicrobial properties for an extended period. The antibacterial silver oxide component and anti-chafing composition can take any form which is typical of dermatological products, for example, hot pour formulations, water-in-oil emulsions, oil-in-water emulsions, gels, sticks, sprays, anhydrous formulations, aerosol formulation, powder form, balms and the like. The composition of the invention may be used as a topical protectant to be applied directly to skin or to objects and materials that come in contact with skin including clothing and footwear, at any time and particularly prior to physical activity by an individual such as before work, play, walking, running, hiking, jogging, etc. The phrase "at any time" is included here because, for example, the composition has use for the relief of bed sores caused by rubbing, as in a hospital, or use against rubbing from ill-fitting footwear for a diabetic, or to help slip-on compression garments.

The composition fulfills a need for an antimicrobial silver oxide containing anti-chafing compound providing the described benefits for a wide range of consumers.

The present invention also relates to an antimicrobial topical composition comprising complexes of chelated silver oxide and a version utilizing chitosan-silver oxide, and in particular to solutions comprising complexed chitosan-silver oxide bio-films, and to the methods of making the same together with anti-chafing compounds.

In one embodiment, the chitosan solution is formed by first providing chitin, which is a homopolymer of beta (1-4)-linked N-acetyl-D-glucosamine. Rinsed, dried and ground chitin can then undergo a process of deacetylation to convert some N-acetyl glucosamine to glucosamine, a primary component of chitosan. The chitosan solution can then be prepared by mixing chitosan with an alpha-hydroxy acid such as glycolic acid and allowing it to thicken. A silver solution can be prepared by mixing silver oxide with a combination of a carboxylic acid and the chitosan solution (such as citric acid) to form silver oxide chelate. Since the chitosan solution is cationic, and the silver solution may be generally neutral, the resulting silver-oxide chitosan complex will be primarily cationic. The cationic solution of the present invention will bond nicely with the generally negatively charged human skin. In use, citrate helps promote uptake of the silver by bacteria.

According to one advantage of the present invention, an antimicrobial solution having high immediate and short term effectiveness is provided. This is accomplished as bacteria are attracted to the citrate in the solution. The citrate promotes uptake of the silver oxide ion in the bacteria, resulting in effective killing of the bacteria. In fact, the present invention comprising the chitosan-silver oxide complex has been evaluated by independent laboratory testing to be effective against salmonella, *e-coli*, MRSA (staph), *pseudomonas aeroginosa*, *serratia marcescens* and *klebsiella pnuemoniae*.

TABLE 1

Silver Oxide Complex Anti-Chafing Compound Combination Test Results for Contact Time for MRSA

| Microorganism | Organism Initial count (CFU/ml) | Control sample Contact time 1 Hr | Test sample Contact time 1 Hr |
|---|---|---|---|
| *S. aureus* (MRSA) ATCC # 43300 | $3.3 \times 10^6$ | $5.2 \times 10^6$ | $4.0 \times 10^2$ |
| % Reduction | — | 0 | 99.99% |
| Log Reduction | — | 0 | 3.92 |

The sample tested (Lot #B0120W02) was 99.9% effective in killing MRSA organisms tested at a 1 hour contact time.

TABLE 2

Silver Oxide Complex Anti-Chafing Compound Combination Test Results for Effectiveness within Specified Application Time

| | Concentration of Organism (CFU/mL) *S. aureus* (MRSA) ATCC # 43300 | | % Reduction | |
|---|---|---|---|---|
| Exposure Time | Control | Product | Control | Product |
| Initial | $6.0 \times 10^5$ | — | — | — |
| 2 min | $5.6 \times 10^5$ | $7.4 \times 10^4$ | 0 | 88% |
| 5 min | $5.8 \times 10^5$ | $2.0 \times 10^4$ | 0 | 97% |
| 10 min | $5.9 \times 10^5$ | $1.9 \times 10^3$ | 0 | 99.7% |

| | Concentration of Organism (CFU/mL) *Escherichia coli* ATCC # 8739 | | % Reduction | |
|---|---|---|---|---|
| Exposure Time | Control | Product | Control | Product |
| Initial | $8.6 \times 10^5$ | — | — | — |
| 2 min | $8.0 \times 10^5$ | $4.2 \times 10^3$ | 0 | 99.5% |
| 5 min | $8.0 \times 10^5$ | $2.2 \times 10^3$ | 0 | 99.7% |
| 10 min | $8.2 \times 10^5$ | 0 | 0 | ≥99.99% |

| | Concentration of Organism (CFU/mL) *Trichophyton mentagrophytes* ATCC # 9533 | | % Reduction | |
|---|---|---|---|---|
| Exposure Time | Control | Product | Control | Product |
| Initial | $2.0 \times 10^5$ | — | — | — |
| 2 min | $2.2 \times 10^5$ | $2.9 \times 10^4$ | 0 | 85% |
| 5 min | $2.7 \times 10^5$ | $1.09 \times 10^4$ | 0 | 94% |
| 10 min | $2.9 \times 10^5$ | $8.3 \times 10^3$ | 0 | 96% |

The sample provided and tested in Table 2 (Lot #B0120W02) above was 99.7% effective in killing MRSA >99.9% effective in killing *E. coli* and 96% effective in killing mentagrophytes organisms within 10 minutes of application time.

TABLE 3

Silver Oxide Complex Anti-Chafing Compound Combination Test Results for Contact Time for *S. aureus* and *Trichophyton mentagrophytes*

| Microorganism | Organism Initial count (CFU/ml) | Control sample Contact time 1 Hr | Test sample Contact time 1 Hr |
|---|---|---|---|
| *S. aureus* (MRSA) ATCC # 43300 | $7.4 \times 10^6$ | $8.5 \times 10^6$ | $2.0 \times 10^5$ |
| % Reduction | — | 0 | 97.3% |
| Log Reduction | — | 0 | 1.6 |
| *Trichophyton mentagrophytes* ATCC # 9533 | $6.6 \times 10^6$ | $8.8 \times 10^6$ | $2.5 \times 10^5$ |
| % Reduction | — | 0 | 96.2% |
| Log Reduction | — | 0 | 1.4 |

The sample provided (Lot #B0110WZ2) was 97.3% effective in killing MRSA and 96.2% effective in killing *T. mentagrophytes* organisms tested at 1 hour contact times.

According to another advantage of the present invention, an antimicrobial solution having high residual effectiveness is provided. This is accomplished as the antimicrobial solution can be prepared to not only be relatively stable but also exhibit low volatility and does not readily evaporate. In part this is due to the hydration of the silver oxide powder in deionized water prior to any chelation and the fact that this causes the silver oxide powder to form a thin and alkaline slurry—again prior to any chlelation and before the addition of the chitosan and carboxylic acid.

Related and according to a further advantage of the present invention, an antimicrobial silver oxide solution that readily bonds to a user's skin such that it remains in place is provided. This is accomplished because in the silver oxide complex of the present invention, the silver oxide is further bonded to the chitosan as a complex and thus forms a molecule that is positively charged or cationic. The skin of the human body typically exhibits a negative charge and accordingly is anionic. The natural electrostatic attraction of the chitosan-silver oxide complex to the surface of the skin allows the complex to bond with the skin. In fact, laboratory results have shown a 75 ppm chitosan-silver oxide complex to have a residual efficacy of two and one half hours under laboratory conditions. This is achieved without the use of synthetic polymers and without the utilization of alcohol, benzalkonium chloride or triclosan. The chelated silver oxide component is the active ingredient that quickly dispatches the bacteria upon contact and also provides unsurpassed biocompatibility qualities not seen for other chelated silver complexes, primarily due to the fact that the silver oxide is stabilized in an alkaline medium prior to chelation and complexing.

According to a still further advantage yet of the present invention, an antimicrobial silver oxide alkaline based solution that is stable, portable and easily dispensable is provided. The stabilization of the silver oxide in an aqueous alkaline medium prior to further complexing provides both instant biocompatibility and antimicrobial action.

According to a still further advantage yet of the present invention, an antimicrobial silver oxide component that is gentle and that does not provide harsh consequences for a user's skin is provided. This is accomplished as the present invention is not known to promote irritation of the skin.

SUMMARY OF THE INVENTION

In one aspect of the invention, a method for reducing chafing to human skin, comprises: topically applying to the human skin a friction-reducing composition, comprising a dermatologically acceptable anhydrous carrier vehicle, wherein the composition, upon topical application onto the skin, leaves a layer on the skin comprising a biofilm of a chelated silver oxide complex.

In a second aspect of the invention, an anti-chafing composition comprises a dermatologically acceptable anhydrous carrier vehicle having suspended therein, wherein the composition, upon topical application onto skin, leaves a layer, comprising an antibacterial-reducing effective amount of the chelated silver oxide particles. Specifically, an antibacterial and anti-chafing barrier composition that comprises both a chelated silver oxide complex and a balm comprising, C18-C36 acid triglycerides, capric/caprylic triglycerides, tribehinin, and allantoin, wherein the chelated silver oxide complex is in a concentration of between 0.1 and 5 weight percent of the total composition such that the balm provides a chafing reducing antibacterial effective layer incorporating chelated silver oxide is provided.

Additionally, the antibacterial chelated silver oxide and anti-chafing composition described above further comprises a dermatologically acceptable carrier selected from the group consisting of organic solutions, gels, liquids, balms, sticks, aerosols, emulsifiers, aqueous lotions, water-in-oil emulsions, oil-in-water emulsions, surfactants, aloe barbadensis leaf juice and tocopheryl acetate.

Other advantages, benefits, and features of the present invention will become apparent to those skilled in the art upon reading the detailed description of the invention and studying the drawings.

BRIEF DESCRIPTION OF THE DRAWINGS

FIG. 1 is a flow chart showing a preferred embodiment of the process of making chitosan from chitin.

FIG. 2 is a flow chart showing a preferred embodiment of the process of making a chitosan solution.

FIG. 3 is a flow chart showing a preferred embodiment of the process of making a silver oxide solution.

FIG. 4 is a flow chart showing a preferred embodiment of the process of preparing the antimicrobial complex of the present invention.

DETAILED DESCRIPTION OF THE PREFERRED EMBODIMENTS

While the invention will be described in connection with one or more preferred embodiments, it will be understood that it is not intended to limit the invention to those embodiments. On the contrary, it is intended to cover all alternatives, modifications and equivalents as may be included within the spirit and scope of the invention as defined by the appended claims.

Looking now to FIG. 1, a process 10 of forming chitosan is provided. Raw material is provided in step 11. The raw material is chitin. Chitin is a homopolymer of beta (1-4)-linked N-acetyl-D-glucosamine. Chitin is an abundant naturally occurring and renewable resource bio-polymer. Chitin is found in exoskeletons of invertebrates. In a preferred embodiment, chitin is derived from the family of decapod crustaceans such as shrimp and prawns. Chitin obtained in this manner generally has a molecular weight of approximately between 500 and 900 kDalton. Process 10 is necessary to the present invention as chitin is insoluble.

The chitin is processed by removing non-chitin components in step 12. This step is accomplished in one embodiment through the use of hydrochloric acid (HCL). The HCL removes or strips any residual meat tissue that is attached to the shell. It is appreciated that other acids or methods of stripping the residual meat tissue can be incorporated without departing from the broad aspects of the present invention. After the residual meat tissue is stripped, a solution of Sodium Hydroxide (NaOH) is used to rinse and neutralize the exoskeletons. In the preferred embodiment, a NaOH solution of approximately 20% is used.

Step 13 involves drying the chitin and processing the chitin to have a desired size. Preferably, the chitin is ground so that it has an average size of approximately 24 mesh (0.0278 inches average particle dimension).

Step 14 is deacetylation. This step 14 involves in a preferred embodiment mixing 1 part chitin with 4 parts 50% NaOH, which is a base to which had been added 1 part of pure water. The resulting mixture comprises 5 parts total, of which the solution has 40% NaOH per 1 part chitin. The mixture is heated to approximately 70 degrees Celsius for about 72 hours to undergo the process of deacetylation. The process of deacetylation converts some of the N-acetyl glucosamine to glucosamine. The result of deacetylation is the aggregation and precipitation of chitosan molecules.

Step 15 is to rinse the chitosan to remove remaining NaOH and any other impurities. In the preferred embodiment, the step 15 of rinsing the chitosan comprises a triple rinse. Yet, it is appreciated that other numbers of rinses could alternatively be used without departing from the broad aspects of the present invention. It is preferable that the chitosan is then allowed to dry. Turning now to FIG. 2, the step 20 of making a 2% chitosan solution is provided.

The following preferred embodiment yields approximately 1 liter, or 1000 mls of the chelated silver oxide complex. The first step (21) in this process (20) is to provide deionized water. 182 ml. of deionized water is measured and placed under moderate to high agitation. 20 grams of chitosan (rinsed and dried) is then provided in step (22), and measured. The chitosan powder is dispersed into and mixed with the deionized water under moderate to high agitation. Next, in step (23), an alpha-hydroxy acid such as glycolic acid is provided. In the preferred embodiment, glycolic acid is used for its lack of strong odor, and is of approximately 70% purity. It is understood that other alpha-hydroxy acids may be used without departing from the broad aspects of the present invention. Approximately 45 ml. of the glycolic acid can be added, and the mixture can be mixed slowly for approximately an additional 45 to 60 minutes. After this period of time, the mixture is preferably viscous. The chitosan solution is preferably ready when it achieves the desired viscosity.

Turning now to FIG. 3, a method (30) of preparing a silver oxide solution is provided. First, in step (31), silver salts can be provided. Primarily, the use of silver oxide in a powdered form is provided. Next, an alkaline aqueous solution of water and the silver oxide powder is provided in step (32). The result, in step (33), is the formation of silver oxide in the form of an aqueous alkaline solution. Once the silver oxide thin slurry is created and fully formed, citric acid can be provided together with the thicker chitosan solution (in step 34), and deionized water can be provided in step 36.

The following steps are utilized to yield a 1 liter, or 1000 ml batch of constituted 1000 ppm chelated silver oxide solution. Slurry 1 is prepared by adding approximately 1.10 grams chelated silver oxide to approximately 198.9 grams distilled water and dispersing for approximately 5-10 minutes. The dispersed chelated silver oxide in water Slurry 1 can be slowly added to a solution of the chitosan and citric acid to form a second solution (2) mixed at a high speed for approximately 30-45 minutes. The resulting silver oxide chelate is colorless and odorless. Remove from agitation, filter through a qualitative analysis filter paper, such as VWR, 415 and set aside in a light impervious container.

The silver is first dispersed in the distilled water to form a thin slurry so that there is a larger exposure of the surface area of the silver to form a silver oxide molecule which can combine with the citric acid. The $Ag_2O$ molecule is only slightly soluble in a solution, hence the addition of citric acid to the mixture also increases solubility with the chitosan to produce a silver ion portion of the silver oxide compound that forms a coordination compound as a result of a Lewis acid-base reaction. The silver ion here is the acid (acceptor) and the chitosan/citric acid solution acts as a ligand base (donor).

In particular the formed solution is a bio-film forming sanitizer that is cationic and bio-adhesive, and contains chelated silver oxide in a concentration sufficient to effect residual antibacterial activity for hours.

The following ratios are used in order to achieve a 1 liter batch, or 1000 ml. batch. First, in steps approximately 500 ml. of 2% chitosan solution and approximately 400 mls. of deionized water are provided which includes citric acid. The chitosan, citric acid and deionized water are preferably mixed slowly for approximately 3 minutes. Next, approximately 100 ml. of the 1000 ppm silver oxide solution is provided. The silver oxide solution is added to the chitosan solution and the solution is preferably mixed slowly for an additional 3 minutes. The resulting solution is a formulation containing 100 ppm silver oxide and bio-bonding chitosan. It is appreciated that all vessels and agitators in this method are made of high density plastic or glass, and must be free of metallic surfaces.

It is understood that other ratios of chitosan solution to silver oxide solution can be used without departing from the broad aspects of the present invention.

The antimicrobial solution of the present invention can be further processed for a wide variety of dispensing methods, but for the purposes of the present invention, dispersion into an anti-chafing balm is provided. This method requires following a procedure such as described in Example 1 which includes adding to the 400 ml of the prepared chelated silver oxide complex, propanediol (and optionally propylene glycol) as a carrier before blending with the anti-chafing balm. The anti-chafing balm comprises; aloe barbadensis leaf juice, C18-C36 acid triglycerides, capric/caprylic triglycerides, tocopheryl acetate, tribehinin, allantoin, and is melted at a temperature of 140-145 degrees Fahrenheit before addition of the chelated silver oxide complex in an amount of between 0.1 to 5 wt. %. The addition of other botanicals such as chamomile can enhance the sensory appeal of the balm. The entire contents are subsequently poured into a plastic container in the shape of a deodorant stick.

In operation, the cationic properties of the solution allow it to bond with a person's or animal's skin, which is negatively charged. It is understood that the general category of animals is intended to include humans.

Yet, according to the present invention, the citrate is complexed with silver ions and silver oxide and chitosan, and the bacteria accordingly take up the silver oxide citrate chitosan complex. Unwanted bacteria, viruses, molds and fungi rapidly die after taking up the silver, as the silver immediately disables vital proteins and the bacteria's metabolic and reproductive functions and the organisms tend to die within minutes. The chelated silver oxide compound, however, provides biocompatibility with desirable cells and organisms such that there are no known toxic side effects when using the chelated silver oxide complex processed as detailed above.

The silver oxide complex is cationic and bonds readily to negatively charged human or animal skin without any toxic effects. The chitosan-silver oxide complex does not cause silver poisoning in a manner such as is known for many of the colloidal (ionic) silver compounds. This is due to the mechanism of the molecule itself. When absorbed into the skin, the complex immediately becomes inert as it binds with free sodium ions that occur naturally in our bodies and on our skin and the oxygen species acts as primarily to promote stable and healthy cell growth. The chelated silver oxide molecule is eventually excreted through the kidneys or out of the pores of the skin depending on the activity level of the individual.

Two examples follow:

Example 1

A 500 ml amount of anti-chafing balm together with 100 ppm of a silver oxide complex was prepared in the following manner:
Solution A
0.265 gms. Citric Acid and add to
299.735 gms. Distilled Water with 2% chitosan solution Mix 5-10 minutes
Slurry 1
0.11 gms. Silver Oxide and add to
99.89 gms. Distilled Water
Disperse 5-10 minutes Take prepared Solution A and place under moderate agitation for the stipulated time. Slowly add the previously dispersed silver oxide in water Slurry 1 and mix at high speed for 30-45 minutes. The resulting silver oxide is a chelate and is colorless and odorless. Remove from agitation, filter through a qualitative analysis filter paper, such as VWR 20 415, and set aside in a light impervious container. The silver oxide complex is now ready to be used with the anti-chafing balm. Take 30 mls of the 2% chitosan solution and to it add 70 mls distilled water. Mix for 1 minute and then add to the 400 mls of the previously prepared 100 ppm chelated silver oxide complex. Mix all for 3 minutes and then add the propanediol (and optionally propylene glycol) as a carrier before blending with the anti-chafing balm. The anti-chafing balm comprises: aloe barbadensis leaf juice, C18-C36 acid triglycerides, capric/caprylic triglycerides, tocopheryl acetate, tribehinin, allantoin, and is melted at a temperature of 140-145 degrees Fahrenheit before addition of the chelated silver oxide complex in an amount of between 0.1 to 5 wt. %. The addition of other botanicals such as chamomile can enhance the sensory appeal of the balm. The entire contents are subsequently poured into a plastic container, such as in the shape of a deodorant stick. The same composition(s) and process could be used in a post addition process as follows: Using the anti-chafe balm, heating it to 140-145 F, causing melting of the balm and introducing the chelated silver oxide complex with propanediol and/or propylene glycol into the melted balm and then subsequently pouring the mixture into a mold and letting the mixture cool to room temperature.

The silver oxide complex described herewithin, also acts as a preservative in that not only does the silver oxide complex provide antimicrobial properties, it also provides stability to the overall composition by incorporating the use of the complexed polymeric chitosan acting as a carrier for the aqueous based complex.

Example 2

The following list of alternative ingredients in the following weight percentages were added in the order shown below in Table 1 to provide the anti-chafing balm (as opposed to the method and composition described in Example 1 above).

TABLE 1

Alternative Order of Addition of Ingredients Required to Prepare Anti-Chafing Balm

| PHASE Number (order of addition) | Ingredient Description | Tradename | Weight Percent | Quantity |
|---|---|---|---|---|
| 100 | CAPRYLIC/CAPRIC TRIGLYCERIDES | RCAPCAP | 51.39990 | 51.40 |
| 101 | ALLANTOIN QA | RALLAN | 0.50000 | 0.50 |
| 102 | DL ALPHA TOCOPHEROL (ANTI-OXIDANT) | RCOVIOXT50 | 0.10000 | 0.10 |
| 103 | OZOKERITE (Melt Pt 75 C.)/117P/SP 1020 | ROZOKERITE | 13.20000 | 13.20 |
| 104 | COMPRITOL 888 ATO | RCOMPRITOL888AT | 2.80000 | 2.80 |
| 105 | CETEARYL ALCOHOL | RCETEARYLALC | 20.00000 | 20.00 |
| 106 | STEARYL ALCOHOL | RSTEARALC | 12.00000 | 12.00 |
| 107 | ALOE VERA OIL | RALOEOIL | 0.00010 | 0.00 |

Phase 100 (the caprylic/capric triglycerides) are first heated to 90 degrees Centigrade and mixing begins with the use of a vortex creating mixer. Phases 101, 102, 103, 104, 105, 106, and 107 are added (preferably) sequentially and cooling to 60 degrees centigrade is allowed during mixing. The batch can then be cooled to room temperature before reheating to accommodate the silver oxide solution or the silver oxide solution can be added prior to cooling back to room temperature. In either case, the result is an antimicrobial silver oxide complex antibacterial anti-chafing composition of the present disclosure.

Once the anti-chafing balm above has been prepared according to the list and phases (order of mixing) provided in Table 1, the same methods described for adding the silver oxide complex as in Example 1, can be employed.

In both examples provided, it is apparent that there has been provided, in accordance with the invention, an antimicrobial silver oxide complex antibacterial anti-chafing composition and methods of making the same that fully satisfies the objects, aims and advantages as set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

We claim:
1. An anti-chafing balm composition comprising:
propanediol and/or propylene glycol;
aloe barbadensis leaf juice, C18-C36 acid triglycerides, capric/caprylic triglycerides, tocopheryl acetate, tribehinin and allantoin;
a stable chelated silver oxide complex having a concentration of at least 100 parts per million (ppm) of silver oxide, wherein said chelated silver oxide complex comprises a mixture of a chitosan solution, a silver solution and carboxylic acid;
wherein said chitosan solution comprises chitosan and glycolic acid; and
wherein said silver solution is a slurry comprising a silver oxide powder in water.

2. The composition of claim 1, wherein said carboxylic acid is citric acid.

3. The composition of claim 2, wherein on a 1000 gram basis, the citric acid is a mixture of approximately 2.65 grams of citric acid and approximately 797.35 grams of water and the chitosan solution, and the silver oxide is in an alkaline slurry that is approximately 1.10 grams silver oxide and approximately 198.9 grams water.

4. The composition of claim 3, wherein said chitosan solution is formed from chitin, said chitin being ground to an average particle diameter of approximately 0.0278 inches.

5. The composition of claim 4, wherein after said chitin is ground to said average particle diameter, said chitin is deacetylated and subsequently mixed with a selected amount of glycolic acid.

6. The composition of claim 1, wherein said anti-chafing balm composition is dispensed via any one of a group consisting of a stick, gel, spray, and an ointment.

7. The composition of claim 1, wherein the anti-chafe balm composition is suitable for being topically applied to human skin, wherein said composition provides continued lubricity and antimicrobial properties for at least 1.5 hours after initial application.

8. The composition of claim 7, wherein said composition further includes glycerin and/or water.

9. A method of creating an antibacterial silver oxide and anti-chafing composition comprising the step of providing a stable chelated silver oxide complex with an anti-chafing balm wherein the anti-chafing balm is heated and then mixed together with said chelated silver oxide complex and the mixture is stirred together at a temperature of at least 140 degrees Fahrenheit;
- wherein the mixture comprises 2-5 wt % of the chelated silver oxide complex;
- wherein said stable chelated silver oxide complex has a concentration of at least 100 parts per million (ppm) of silver oxide and comprises a mixture of a chitosan solution, carboxylic acid and a silver solution is a slurry comprising water and powdered silver oxide;
- wherein said chitosan solution comprises chitosan and glycolic acid;
- wherein said silver oxide chitosan complex is a cationic solution;
- and wherein the anti-chafing balm consists essentially of:
    - propanediol and/or propylene glycol; and
    - aloe barbadensis leaf juice, C18-C36 acid triglycerides, capric/caprylic triglycerides, tocopheryl acetate, tribehinin and allantoin.

10. The method of claim 8, wherein said chelated silver oxide complex has a residual efficacy of at least 1.5 hours when applied to skin.

11. A method of reducing bacteria on and chafing of human skin, comprising topically applying to human skin the composition of claim 1.

12. The method of claim 11, wherein the composition further comprises a dermatologically acceptable anhydrous carrier vehicle, selected from the group consisting of organic solutions, gels, liquids, aerosols, emulsifiers, lotions, water-in-oil emulsions, oil-in-water emulsions, and surfactants.

* * * * *